United States Patent
Pedersen et al.

(10) Patent No.: US 9,149,044 B2
(45) Date of Patent: Oct. 6, 2015

(54) PESTICIDAL COMPOSITIONS

(75) Inventors: Palle Pedersen, Stanton, MN (US); Clifford George Watrin, Minnetonka, MN (US); Michael Oostendorp, Stein (CH); Andre Luiz-Freitas de Oliveira, Greensboro, NC (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 14/009,193

(22) PCT Filed: Apr. 13, 2012

(86) PCT No.: PCT/EP2012/056806
§ 371 (c)(1),
(2), (4) Date: Dec. 5, 2013

(87) PCT Pub. No.: WO2012/140212
PCT Pub. Date: Oct. 18, 2012

(65) Prior Publication Data
US 2014/0228212 A1    Aug. 14, 2014

Related U.S. Application Data

(60) Provisional application No. 61/475,863, filed on Apr. 15, 2011.

(51) Int. Cl.
*A01N 63/02* (2006.01)
*A01N 63/00* (2006.01)
*A01N 51/00* (2006.01)

(52) U.S. Cl.
CPC ............. *A01N 63/02* (2013.01); *A01N 63/00* (2013.01)

(58) Field of Classification Search
CPC ........ A01N 63/00; A01N 63/02; A01N 51/00
USPC ................. 424/405, 93.1, 93.3, 93.4, 93.5; 504/100, 101, 189
See application file for complete search history.

(56) References Cited

U.S. PATENT DOCUMENTS

2010/0034792 A1* 2/2010 Becker .................. 424/93.46

FOREIGN PATENT DOCUMENTS

| EP | 0214427 | 3/1987 | |
|----|---------|--------|---|
| EP | 0217378 | 8/1987 | |
| EP | 0217378 A1 * | 8/1987 | ............. A01N 63/00 |
| WO | 2010/084194 | 7/2007 | |
| WO | 2007/149817 | 12/2007 | |
| WO | 2009/060012 | 5/2009 | |
| WO | 2009/124707 | 10/2009 | |
| WO | 2009/126473 | 10/2009 | |
| WO | WO2009/124707 A2 * | 10/2009 | ............. A01N 63/00 |
| WO | 2010/030554 | 3/2010 | |
| WO | WO2010/030554 A1 * | 3/2010 | ............. C12N 15/87 |
| WO | WO2010/084194 A1 * | 7/2010 | ............. A01N 63/00 |

OTHER PUBLICATIONS

International Search Report from International Application No. PCT/EP2012/056806 mailed Mar. 4, 2013.

* cited by examiner

*Primary Examiner* — Jane C Oswecki
(74) *Attorney, Agent, or Firm* — Brian D. McAlhaney

(57) ABSTRACT

Combinations suitable for agricultural use can include (I) a nematode-antagonistic biocontrol agent and (II) one or more agents selected, independently of each other, from any one of (A) to (H): (A) at least one fungicide; (B) at least one insecticide; (C) at least one synthetic nematicide; (D) bacterium of the genus *Bacillus*; (E) Harpin; (F) Isoflavones; (G) Plant growth regulators; and/or (H) Plant activators.

5 Claims, No Drawings

PESTICIDAL COMPOSITIONS

This application is a 371 of International Application No. PCT/EP2012/056806 filed Apr. 13, 2012 which claims priority to U.S. Provisional Patent Application No. 61/475,863 filed Apr. 15, 2011, to which the contents of all are incorporated herein by reference.

FIELD OF TECHNOLOGY

The present disclosure relates generally to the use of nematode-antagonistic biocontrol agents, and more particularly, to combinations of at least one nematode-antagonistic biocontrol agent and one or more defined agents. Methods of using these may include, for example, methods in agriculture to improve the growing characteristics of a plant. Methods for using such combinations may also include, control of damage by pests, such as insect, nematode and pathogen, especially in the agricultural field.

BACKGROUND

A variety of different active ingredients, agents and combinations are described in the literature for, inter alia, improving plant growth; however, such known uses do not always satisfy the needs of agricultural practice in many incidents and aspects. There is a continuing need to provide improved combinations, which may provide better, for example, biological properties, e.g., synergistic properties, especially for controlling pests. Further, biological properties of known combinations are not always entirely satisfactory in the areas of pest control, phytotoxicity, and environmental and worker exposure, for example. In particular, in the instance a pest has become, or risks becoming resistant to the known compositions or active ingredients, improved methods of control or prevention are sought.

One such pest known to damage crops is the nematode. There are many types of nematode pests, one such nematode is the soybean cyst nematode (SCN), *Heterodera glycines* Ichinohe. SCN causes substantial losses in soybean production. Yield suppression attributed to *H. glycines* alone resulted in an estimated $750 million in losses to U.S. soybean producers annually from 2003 to 2005 (Wrather, J. A., and Koerining, S. R., Estimates of disease effects on soybean yields in the United States 2003 to 2005, J. Nematol. 38:173-180, 2006).

In light of the methods currently used to control pests, for example, nematode pests, applicants believe there remains a further need for increased pest control. Applicants also desire to reduce the rate at which pests acquire an increasing tolerance to both pest resistant crop plants and pesticides. Applicants also desire to extend the useful life of both pest resistant crop plants and pesticides. Various aspects of the instant disclosure may be directed to at least one of the above mentioned, or additional, problems.

SUMMARY

By way of summary, the present technology includes combinations of at least one nematode-antagonistic biocontrol agent and one or more defined agents. The defined agents may include agents that provide growing characteristics to a plant through control of pests, e.g., through making available nutrients, through activating the plant growth properties, e.g. natural defense mechanism, and the like. The disclosed combinations may, in some examples, provide unexpected control or prevention of damage by pests to a plant, when the particular ingredients of the defined combination is applied, in any desired sequence or simultaneously, on the plant, part of a plant, plant organ, and/or plant propagation material thereof, or surrounding area thereof.

Accordingly, the present disclosure provides, inter alia, a combination, particularly a pesticidal combination, suitable for agricultural use comprising (I) at least one nematode-antagonistic biocontrol agent and (II) one or more agents selected, independently of each other, from any one of (A) to (H):

(A) at least one fungicide;
(B) at least one insecticide;
(C) at least one synthetic nematicide;
(D) bacterium of the genus *Bacillus*;
(E) Harpin;
(F) Isoflavones;
(G) Plant growth regulators; and/or
(H) Plant activators.

In a second aspect, the present technology provides a method of controlling or preventing pest damage in a plant propagation material, a plant, part of a plant and/or plant organ that grow at a later point in time, which comprises applying on the pest, plant, part of the plant, plant organ, plant propagation material or a surrounding area thereof, a combination comprising (I) at least one nematode-antagonistic biocontrol agent and (II) one or more agents selected, independently of each other, from any one of (A) to (H), in any desired sequence or simultaneously.

In a third aspect, the present technology provides a method of protecting a plant propagation material, a plant, part of a plant and/or plant organ that grow at a later point in time against pest damage by applying to the pest, plant, part of plant, plant organ, plant propagation material or a surrounding area thereof a combination comprising (I) at least one nematode-antagonistic biocontrol agent and (II) one or more agents selected, independently of each other, from any one of (A) to (H), in any desired sequence or simultaneously.

In an embodiment, the present technology includes a method of protecting a plant propagation material, a plant, part of a plant and/or plant organ that grow at a later point in time against pest damage by applying to the plant propagation material the ingredients of the combination, comprising (I) at least one nematode-antagonistic biocontrol agent and (II) one or more agents selected, independently of each other, from any one of (A) to (H), in any desired sequence or simultaneously.

The present technology also relates to a plant propagation material treated with the combination, comprising (I) at least one nematode-antagonistic biocontrol agent and (II) one or more agents selected, independently of each other, from any one of (A) to (H), in any desired sequence or simultaneously.

Further, in an embodiment the present technology relates to a method which comprises (i) treating a plant propagation material, such as a seed, with the combination, comprising (I) at least one nematode-antagonistic biocontrol agent and (II) one or more agents selected, independently of each other, from any one of (A) to (H), in any desired sequence or simultaneously, and (ii) planting or sowing the treated propagation material, wherein the combination protects against pest damage of the treated plant propagation material, or part of plant, plant organ and/or plant grown from the treated propagation material.

Also, in an embodiment the present technology relates to a method which comprises (i) treating a plant propagation material, such as a seed, with the combination, comprising (I) at least one nematode-antagonistic biocontrol agent and (II) one or more agents selected, independently of each other, from any one of (A) to (H), in any desired sequence or simultaneously, and (ii) planting or sowing the treated propagation material, and (iii) achieving protection against pest damage of the treated plant propagation material, or part of plant, plant organ and/or plant grown from the treated propagation material.

The above was intended to summarize certain aspects of various embodiments of the present disclosure. Combinations and methods will be set forth in more detail, along with examples demonstrating efficacy, in the data and detailed description below. It will be apparent, however, that the detailed description is not intended to limit the present invention.

DETAILED DESCRIPTION OF EXEMPLARY EMBODIMENTS

Nematode-antagonistic biocontrol agents suitable for use in the present technology include nematophagous fungi and nematophagous bacteria. The term "nematode-antagonistic biocontrol agent" as used herein refers to an organism that inhibits nematode activity, growth or reproduction, or reduces nematode-related disease in plants, or which releases or contains substances toxic or inhibitory to nematodes.

Nematophagous fungi useful herein include, but are not limited to, *Arthrobotrys* spp., for example, *Arthrobotrys oligospora*, *Arthrobotrys superb* and *Arthrobotrys dactyloides*; *Dactylaria* spp., for example, *Dactylaria candida*; *Harposporium* spp., for example, *Harposporium anguillulae*; *Hirsutella* spp., for example, *Hirsutella rhossiliensis* and *Hirsutella minnesotensis*, *Monacrosporium* spp., for example, *Monacrosporium cionopagum*; *Nematoctonus* spp., for example, *Nematoctonus geogenius*, *Nematoctonus leiosporus*; *Meristacrum* spp., for example, *Meristacrum asterospermum*; *Harposporium* spp., for example, *Harposporium anguillulae*; *Paecilomyces* spp., for example, *Paecilomyces lilacinus*; *Pochonia* spp., for example, *Pochonia chlamydopora* and *Streptomyces* spp.

Nematophagous bacteria useful herein include, but are not limited to, obligate parasitic bacteria, opportunistic parasitic bacteria, rhizobacteria, parasporal Cry protein-forming bacteria, endophytic bacteria and symbiotic bacteria. In particular embodiments, the biocontrol agent can be a bacteria species selected from *Actinomycetes* spp., *Agrobacterium* spp., *Allorhizobium* spp., *Arthrobacter* spp., *Alcaligenes* spp., *Aureobacterium* spp., *Azobacter* spp., *Azorhizobium* spp., *Azospirillium* spp., *Beijerinckia* spp., *Bradyrhizobium* spp., *Burkholderia* spp., *Chromobacterium* spp., *Clavibacter* spp., *Clostridium* spp., *Comomonas* spp., *Corynebacterium* spp., *Curtobacterium* spp., *Desulforibtio* spp., *Enterobacter* spp., *Flavobacterium* spp., *Gluconobacter* spp., *Hydrogenophage* spp., *Klebsiella* spp., *Methylobacterium* spp., *Phyllobacterium* spp., *Phingobacterium* spp., *Photorhabdus* spp., *Rhizobium* spp., *Serratia* spp., *Stenotrotrophomonas* spp., *Xenorhabdus* spp. *Variovorax* spp., *Pasteuria* spp., *Pseudomonas* spp., and *Paenibacillus* spp.

Preferred nematode-antagonistic biocontrol agents include ARF18; *Arthrobotrys* spp.; *Chaetomium* spp.; *Cylindrocarpon* spp.; *Exophilia* spp.; *Fusarium* spp.; *Gliocladium* spp.; *Hirsutella* spp.; *Lecanicillium* spp.; *Monacrosporium* spp.; *Myrothecium* spp.; *Neocosmospora* spp.; *Paecilomyces* spp.; *Pochonia* spp.; *Stagonospora* spp.; vesicular-arbuscular mycorrhizal fungi, *Burkholderia* spp.; *Pasteuria* spp., *Brevibacillus* spp.; *Pseudomonas* spp.; and Rhizobacteria.

Particularly preferred nematode-antagonistic biocontrol agents include ARF18, *Arthrobotrys oligospora*, *Arthrobotrys dactyloides*, *Chaetomium globosum*, *Cylindrocarpon heteronema*, *Exophilia jeanselmei*, *Exophilia pisciphila*, *Fusarium aspergilus*, *Fusarium solani*, *Gliocladium catenulatum*, *Gliocladium roseum*, *Gliocladium vixens*, *Hirsutella rhossiliensis*, *Hirsutella minnesotensis*, *Lecanicillium lecanii*, *Monacrosporium drechsleri*, *Monacrosporium gephyropagum*, *Myrotehcium verrucaria*, *Neocosmospora vasinfecta*, *Paecilomyces lilacinus*, *Pochonia chlamydosporia*, *Stagonospora heteroderae*, *Stagonospora phaseoli*, vesicular-arbuscular mycorrhizal fungi, *Burkholderia cepacia*, *Pasteuria penetrans*, *Pasteuria thornei*, *Pasteuria nishizawae*, *Pasteuria ramosa*, *Pastrueia usage*, *Brevibacillus laterosporus* strain G4, *Pseudomonas fluorescens* and Rhizobacteria.

The present technology provides a combination, particularly a pesticidal combination, suitable for agricultural use comprising (I) at least one nematode-antagonistic biocontrol agent, described above, and (II) one or more agents selected, independently of each other, from any one of (A) to (H).

The fungicides, (A), suitable for use herein include at least one member selected from the group consisting of amisulbrom, azoxystrobin, boscalid, captan, carboxin, cyproconazole, cyprodinil, difenoconazole, dimoxystrobin, enestrobin, fludioxonil, fluopyram, fluoxastrobin, fluquinconazole, flutriafol, fuberidazole, flutriafol, fluxapyroxad, ipconazole, mancozeb, mefenoxam, metalaxyl, myclobutanil, penflufen, penthiopyrad, prochloraz, prothioconazole, pyraclostrobin, pyribencarb, sedaxane, SYP-1620, SYP-Z048 tebuconazole, thiabendazole, thiophanate-methyl, thiram, triadimenol, triazoxide, trifloxystrobin and triticonazole.

The insecticides, (B), suitable for use include at least one member selected from the group consisting of thiamethoxam, clothianidin, imidacloprid, thiacloprid, acetamiprid, beta-cyfluthrin, cyantraniliprole, diafenthiuron, diazinon, emamectin (benzoate), fenoxycarb, fipronil, flonicamid, lambda-cyhalothrin, lufenuron, methiocarb, pymetrozine, pyriproxyfen, pyrifluquinazon, spinetoram, spinosad, spirotetramat, tefluthrin, thiodicarb or Ti-435.

The synthetic nematicides, (C), suitable for use herein include at least one member selected from the group consisting of avermectin nematicides, such as abamectin; carbamate nematicides, such as, aldicarb, thiadicarb, carbofuran, carbosulfan, oxamyl, aldoxycarb, ethoprop, methomyl, benomyl, alanycarb; and organophosphorus nematicides, such as, fenamiphos, fensulfothion, terbufos, fosthiazate, dimethoate, phosphocarb, dichlofenthion, isamidofos, fosthietan, isazofos ethoprophos, cadusafos, terbufos, chlorpyrifos, dichlofenthion, heterophos, isamidofos, mecarphon, phorate, thionazin, triazophos, diamidafos, fosthietan and phosphamidon.

Bacterium of the genus *Bacillus*, (D), suitable for use herein include at least one member selected from the group consisting of *Bacillus* sp B16, *Bacillus agri*, *Bacillus aizawai*, *Bacillus albolactis*, *Bacillus amyloliquefaciens*, *Bacillus cereus*, *Bacillus firmus*, *Bacillus coagulans*, *Bacillus endoparasiticus*, *Bacillus endorhythmos*, *Bacillus firmus*, *Bacillus kurstaki*, *Bacillus lacticola*, *Bacillus lactimorbus*, *Bacillus lactis*, *Bacillus laterosporus*, *Bacillus lentimorbus*, *Bacillus licheniformis*, *Bacillus megaterium*, *Bacillus medusa*, *Bacillus metiens*, *Bacillus natto*, *Bacillus nigrificans*, *Bacillus popillae*, *Bacillus pumilus*, *Bacillus siamensis*, *Bacillus sphaericus*, *Bacillus* spp., *Bacillus subtilis*, *Bacillus thuringiensis* (including those forming Cry proteins toxic to nematodes and/or nematode larvae such as Cry5, Cry6, Cry12, Cry13, Cry14 and Cry21), *Bacillus thuringiensis israelensis*; *Bacillus thuringiensis kurstaki*, *Bacillus uniflagellates*, plus those listed in the category of Bacillus Genus in the "Bergey's Manual of Systematic Bacteriology, First Ed. (1986)" alone or in combination. In a particularly preferred embodiment, the bacterium of the genus *Bacillus* comprises is at least one *B. firmus* CNCM I-1582 spore and/or *B. cereus* strain CNCM I-1562 spore as disclosed in U.S. Pat. No. 6,406,690, which is incorporated herein by reference in its entirety. In other preferred embodiments, the bacteria is at least one *B. amyloliquefaciens* IN937a, at least one *Bacillus subtilis* strain designation GB03, or at least one *B. pumilus* strain designation GB34. Combinations of the four species of above-listed bacteria, as well as other spore-forming, root-colonizing bacteria known to exhibit agriculturally beneficial properties are within the scope and spirit of the present invention. Particularly preferred embodiments according to the invention are also those compositions that comprise mutants of *B. firmus* CNCM I-1582 spore and/or *B. cereus* strain CNCM I-1562 spore. Very particularly preferred are those mutants that have a nematicidal activity.

Harpin (E), (CAS RN 151438-54-9) is a protein produced by the plant pathogenic bacterium, *Erwinia amylovora*. It is available under the brand Messenger™. It is described in U.S. Pat. No. 5,849,868 and U.S. Pat. No. 5,776,889. Harpin was disclosed as a plant activator, for example, in WO 95/31564. In some instances, Harpin is known to have nematicidal characteristics and accordingly in such instances, the present invention also relates to combinations which contain Harpin.

Isoflavones, (F), are preferably formononetin and gengenistein, biochanin A, daidzein, glycitein, hesperetin, naringenin, chalcone, coumarin, Ambiol (2-methyl-4-[dimethylaminomethyl]-5-hydroxybenzimidazole), ascorbate and pratensein and the salts and esters thereof.

Plant growth regulator (G) include paclobutrazol, trinexapac-ethyl, and gibberellins GA3, GA7 or a mixture thereof.

Plant activators, (H), include acibenzolar-S-methyl and probenazole.

In an embodiment of any aspects of the invention, the combination is a composition comprising, preferably of, (I) a nematode-antagonistic biocontrol agent and (II) one or more pesticidal agents selected from (A) amisulbrom, azoxystrobin, boscalid, captan, carboxin, cyproconazole, cyprodinil, difenoconazole, dimoxystrobin, enestrobin, fludioxonil, fluopyram, fluoxastrobin, fluquinconazole, flutriafol, fuberidazole, flutriafol, ipconazole, mancozeb, mefenoxam, metalaxyl, myclobutanil, penflufen, penthiopyrad, prochloraz, prothioconazole, pyraclostrobin, pyribencarb, sedaxane, SYP-1620, SYP-Z048 tebuconazole, thiabendazole, thiophanate-methyl, thiram, triadimenol, triazoxide, trifloxystrobin and triticonazole, and optionally (III) one or more customary formulation auxiliaries.

In an embodiment of any aspects of the invention, the combination is a composition comprising, preferably of, (I) a nematode-antagonistic biocontrol agent and (II) one or more pesticidal agents selected from (B) thiamethoxam, clothianidin, imidacloprid, thiacloprid, acetamiprid, beta-cyfluthrin, cyantraniliprole, diafenthiuron, diazinon, emamectin, emamectin benzoate, fenoxycarb, fipronil, flonicamid, lambda-cyhalothrin, methiocarb, pymetrozine, pyriproxyfen, pyrifluquinazon, spinetoram, spinosad, spirotetramat, tefluthrin, thiodicarb or Ti-435, and optionally (III) one or more customary formulation auxiliaries.

In an embodiment of any aspects of the invention, the combination is a composition comprising, preferably of, (I) a nematode-antagonistic biocontrol agent and (II) one or more pesticidal agents selected from (C) at least one synthetic nematicide selected from the group consisting of an avermectin, such as abamectin; carbamate nematicides, such as, aldicarb, thiadicarb, carbofuran, carbosulfan, oxamyl, aldoxycarb, ethoprop, methomyl, benomyl, alanycarb; and organophosphorus nematicides, such as, fenamiphos, fensulfothion, terbufos, fosthiazate, dimethoate, phosphocarb, dichlofenthion, isamidofos, fosthietan, isazofos ethoprophos, cadusafos, terbufos, chlorpyrifos, dichlofenthion, heterophos, isamidofos, mecarphon, phorate, thionazin, triazophos, diamidafos, fosthietan and phosphamidon.

In an embodiment of any aspects of the invention, the combination is a composition comprising, preferably of, (I) a nematode-antagonistic biocontrol agent and (II) (E) harpin, and optionally (III) one or more customary formulation auxiliaries.

In an embodiment of any aspects of the invention, the combination is a composition comprising, preferably of, (I) a nematode-antagonistic biocontrol agent and (II) (D) *Bacillus firmus* strain 1-1582, and optionally (III) one or more customary formulation auxiliaries.

In an embodiment of any aspects of the invention, the combination is a composition comprising, preferably of, (I) a nematode-antagonistic biocontrol agent and (II) one or more agents selected from (F) Formononetin and Genistein, and optionally (III) one or more customary formulation auxiliaries.

In an embodiment of any aspects of the invention, the combination is a composition comprising, preferably of, (I) a nematode-antagonistic biocontrol agent and (II) one or more agents selected from (G) a plant growth regulator, such as paclobutrazol, trinexapac-ethyl, and gibberellins GA3, GA7 or a mixture thereof, and optionally (III) one or more customary formulation auxiliaries.

In an embodiment of any aspects of the invention, the combination is a composition comprising, preferably of, (I) a nematode-antagonistic biocontrol agent and (II) one or more agents selected from (G) a plant activator and optionally (III) one or more customary formulation auxiliaries.

A particularly preferred combination is one selected from (I) a nematode-antagonistic biocontrol agent and (II) a mixture of (B) one or more of thiamethoxam, clothianidin, imidacloprid, cyantraniliprole, lambda-cyhalothrin, spinosad, spirotetramat, tefluthrin or thiodicarb, and (A) one or more of azoxystrobin, trifloxystrobin, fluoxastrobin, cyproconazole, difenoconazole, prothioconazole, tebuconazole, triticonazole, fludioxonil, thiabendazole, ipconazole, cyprodinil, myclobutanil, metalaxyl, mefenoxam or sedaxane.

In an embodiment the combination is one selected from (I) a nematode-antagonistic biocontrol agent and (II) a mixture of (B) thiamethoxam, and (A) one or more of amisulbrom, azoxystrobin, boscalid, captan, cyproconazole, cyprodinil, difenoconazole, dimoxystrobin, enestrobin, fludioxonil, fluopyram, fluoxastrobin, ipconazole, mefenoxam, metalaxyl, myclobutanil, penflufen, penthiopyrad, prothioconazole, pyraclostrobin, pyribencarb, sedaxane, SYP-1620, SYP-Z048 tebuconazole, thiabendazole, thiophanate-methyl, trifloxystrobin, triticonazole.

In an embodiment the combination is one selected from (I) a nematode-antagonistic biocontrol agent and (II) a mixture of (C) abamectin and (A) one or more of amisulbrom, azoxystrobin, boscalid, captan, carboxin, cyproconazole, cyprodinil, difenoconazole, dimoxystrobin, enestrobin, fludioxonil, fluopyram, fluoxastrobin, fluquinconazole, flutriafol, fuberidazole, flutriafol, ipconazole, mancozeb, mefenoxam, metalaxyl, myclobutanil, penflufen, penthiopyrad, prochloraz, prothioconazole, pyraclostrobin, pyribencarb, sedaxane, SYP-1620, SYP-Z048 tebuconazole, thiabendazole, thiophanate-methyl, thiram, triadimenol, triazoxide, trifloxystrobin and triticonazole.

In an embodiment the combination is one selected from (I) a nematode-antagonistic biocontrol agent and (II) a mixture of (B) lambda-cyhalothrin, and (A) one or more of amisulbrom, azoxystrobin, boscalid, captan, carboxin, cyproconazole, cyprodinil, difenoconazole, dimoxystrobin, enestrobin, fludioxonil, fluopyram, fluoxastrobin, fluquinconazole, flutriafol, fuberidazole, flutriafol, ipconazole, mancozeb, mefenoxam, metalaxyl, myclobutanil, penflufen, penthiopyrad, prochloraz, prothioconazole, pyraclostrobin, pyribencarb, sedaxane, SYP-1620, SYP-Z048 tebuconazole, thiabendazole, thiophanate-methyl, thiram, triadimenol, triazoxide, trifloxystrobin and triticonazole.

In an embodiment the combination is one selected from (I) a nematode-antagonistic biocontrol agent and (II) a mixture of (B) tefluthrin, and (A) one or more of amisulbrom, azoxystrobin, boscalid, captan, carboxin, cyproconazole, cyprodinil, difenoconazole, dimoxystrobin, enestrobin, fludioxonil, fluopyram, fluoxastrobin, fluquinconazole, flutriafol, fuberidazole, flutriafol, ipconazole, mancozeb, mefenoxam, metalaxyl, myclobutanil, penflufen, penthiopyrad, prochloraz, prothioconazole, pyraclostrobin, pyribencarb, sedaxane, SYP-1620, SYP-Z048 tebuconazole, thiabendazole, thiophanate-methyl, thiram, triadimenol, triazoxide, trifloxystrobin and triticonazole.

In an embodiment the combination comprises (I) a nematode-antagonistic biocontrol agent and (II) a mixture of (B) thiamethoxam and (B) one or more of lambda-cyhalothrin, tefluthrin, fipronil. In a further embodiment, the combination comprises (I) a nematode-antagonistic biocontrol agent and (II) a mixture of (B) thiamethoxam and (B) one or more of lambda-cyhalothrin, tefluthrin, fipronil, and optionally one or more compounds selected from (A) amisulbrom, azoxystrobin, boscalid, captan, carboxin, cyproconazole, cyprodinil, difenoconazole, dimoxystrobin, enestrobin, fludioxonil, fluopyram, fluoxastrobin, fluquinconazole, flutriafol, fuberidazole, flutriafol, ipconazole, mancozeb, mefenoxam, metalaxyl, myclobutanil, penflufen, penthiopyrad, prochloraz, prothioconazole, pyraclostrobin, pyribencarb, sedaxane, SYP-1620, SYP-Z048 tebuconazole, thiabendazole, thiophanate-methyl, thiram, triadimenol, triazoxide, trifloxystrobin and triticonazole.

In an embodiment the combination comprises (I) a nematode-antagonistic biocontrol agent, (B) thiamethoxam, and (C) abamectin.

In an embodiment the combination comprises (I) a nematode-antagonistic biocontrol agent, (B) one or more of clothianidin and thiodicarb, and (C) abamectin.

Examples of preferred mixtures comprise a (I) nematode-antagonistic biocontrol agent and any one of a)-dd):
a) abamectin;
b) acibenzolar-S-methyl;
c) azoxytrobin;
d) *Bacillus firmus;*
e) clothianidin;
f) cyproconazole;
g) difenoconazole;
h) fludioxonil;
i) fluoxastrobin;
j) fluxapyroxad;
k) Harpin;
l) imidacloprid;
m) mefenoxam;
n) metalaxyl;
o) paclobutrazole;
p) penflufen;
q) prochloraz;
r) prothioconazole;
s) pyraclostrobin;
t) pyrimiphos-methyl;

u) sedaxane;
v) spinetoram;
w) spinosad;
x) spirotetramat;
y) tebuconazole;
z) tefluthrin;
aa) thiamethoxam;
bb) thiabendazole;
cc) trinexapac-ethyl;
dd) triticonazole;
wherein (I) is selected from the group consisting of *Arthrobotrys* spp., *Chaetomium* spp., *Hirsutella* spp., *Pasteuria* spp., *Pochonia* spp., *Pseudomonas* spp., and Rhizobacteria. Preferably (I) is selected from the group consisting of *Hirsutella* spp., *Paecilomyces* spp., *Pasteuria* spp., *Pochonia* spp., *Pseudomonas* spp., and Rhizobacteria. More preferably (I) is selected from the group consisting of *Hirsutella rhossiliensis, Hirsutella minnesotensis, Pasteuria penetrans, Pasteuria thornei, Pasteuria nishizawae, Pseudomonas fluorescens* and Rhizobacteria.

Examples of mixtures comprising 3 or more active ingredients include compositions comprising a (I) nematode-antagonistic biocontrol agent and any one of a)-jj):
a) abamectin+thiamethoxam;
b) *Bacillus* spp.+thiodicarb and/or clothianidin;
c) *Bacillus firmus*+thiodicarb and/or clothianidin;
d) clothianidin+harpin;
e) clothainidin+imidacloprid;
f) clothianidin+beta-cyfluthrin;
g) clothianidin+fipronil;
h) clothianidin+tefluthrin;
i) clothianidin+thiodicarb;
j) cyproconazole+fludioxonil;
k) fludioxonil+azoxystrobin;
l) fludioxonil+azoxystrobin+mefenoxam;
m) fludioxonil+azoxystrobin+metalaxyl;
n) fludioxonil+difenoconazole;
o) fludioxonil+mefenoxam;
p) fludioxonil+metalaxyl;
q) fludioxonol+triticonazole;
r) fluoxastrobin+prothioconazole;
s) imidacloprid+fipronil;
t) imidacloprid+harpin;
u) imidacloprid+thiodicarb;
v) imidacloprid+tefluthrin;
w) prothioconazole+tebuconazole+triazoxide;
x) prothioconazole+tebuconazole;
y) sedaxane+azoxystrobin;
z) sedaxane+fludioxonil;
aa) sedaxane+mefenoxam;
bb) sedaxane+metalaxyl;
cc) sedaxane+thiabendazole;
dd) sedaxane+thiamethoxam;
ee) thiabendazole+azoxystrobin;
ff) thiabendazole+mefenoxam;
gg) thiabendazole+metalaxyl;
hh) thiabendazole+thiamethoxam;
ii) thiamethoxam+mefenoxam+fludioxonil;
jj) thiamethoxam+metalaxyl+fludioxonil;
wherein (I) is selected from the group consisting of *Arthrobotrys* spp., *Chaetomium* spp., *Hirsutella* spp., *Pasteuria* spp., *Pochonia* spp., *Pseudomonas* spp., and Rhizobacteria. Preferably (I) is selected from the group consisting of *Hirsutella* spp., *Paecilomyces* spp., *Pasteuria* spp., *Pochonia* spp., *Pseudomonas* spp., and Rhizobacteria. More preferably (I) is selected from the group consisting of *Hirsutella rhossiliensis,*

*Hirsutella minnesotensis, Pasteuria penetrans, Pasteuria thornei, Pasteuria nishizawae, Pseudomonas fluorescens* and Rhizobacteria.

Each combination according to the invention is especially advantageous for the treatment of plant propagation material. Examples of specific combinations encompassed by the invention include, but are not limited to:

| Nematode-antagonistic biocontrol agent | Other agent(s) |
|---|---|
| *Hirsutella* spp. | azoxystrobin, cyproconazole, difenoconazole, fludioxonil, mefenoxam, metalaxyl, paclobutrazol, prothioconazole, sedaxane, tebuconazole, thiabendazole and/or triticonazole |
| *Hirsutella* spp. | thiamethoxam, clothianidin, cyantraniliprole, diafenthiuron, emamectin, imidacloprid, lambda-cyhalothrin, lufenuron, pirimicarb, profenofos, pymetrozine, spinetoram, spinosad, spirotetramat, tefluthrin and/or thiodicarb |
| *Hirsutella* spp. | abamectin and/or fosthiazate |
| *Hirsutella* spp. | *Bacillus* spp. |
| *Pseudomonas fluorescens* | azoxystrobin, cyproconazole, difenoconazole, fludioxonil, mefenoxam, metalaxyl, paclobutrazol, prothioconazole, sedaxane, tebuconazole, thiabendazole and/or triticonazole |
| *Pseudomonas fluorescens* | thiamethoxam, clothianidin, cyantraniliprole, diafenthiuron, emamectin, imidacloprid, lambda-cyhalothrin, lufenuron, pirimicarb, profenofos, pymetrozine, spinetoram, spinosad, spirotetramat, tefluthrin and/or thiodicarb |
| *Pseudomonas fluorescens* | abamectin and/or fosthiazate |
| *Pseudomonas fluorescens* | *Bacillus* spp. |
| *Pasteuria* spp. | azoxystrobin, cyproconazole, difenoconazole, fludioxonil, mefenoxam, metalaxyl, paclobutrazol, prothioconazole, sedaxane, tebuconazole, thiabendazole and/or triticonazole |
| *Pasteuria* spp. | thiamethoxam, clothianidin, cyantraniliprole, diafenthiuron, emamectin, imidacloprid, lambda-cyhalothrin, lufenuron, pirimicarb, profenofos, pymetrozine, spinetoram, spinosad, spirotetramat, tefluthrin and/or thiodicarb |
| *Pasteuria* spp. | abamectin and/or fosthiazate |
| *Pasteuria* spp. | *Bacillus* sp B16 |
| *Pasteuria* spp. | *Bacillus agri* |
| *Pasteuria* spp. | *Bacillus aizawai* |
| *Pasteuria* spp. | *Bacillus albolactis* |
| *Pasteuria* spp. | *Bacillus amyloliquefaciens* |
| *Pasteuria* spp. | *Bacillus cereus* |
| *Pasteuria* spp. | *Bacillus coagulans* |
| *Pasteuria* spp. | *Bacillus endoparasiticus* |
| *Pasteuria* spp. | *Bacillus endorhythmos* |
| *Pasteuria* spp. | *Bacillus firmus* |
| *Pasteuria* spp. | *Bacillus kurstaki* |
| *Pasteuria* spp. | *Bacillus Iacticola* |
| *Pasteuria* spp. | *Bacillus lactimorbus* |
| *Pasteuria* spp. | *Bacillus lactis* |
| *Pasteuria* spp. | *Bacillus laterosporus* |
| *Pasteuria* spp. | *Bacillus lactimorbus* |
| *Pasteuria* spp. | *Bacillus licheniformis* |
| *Pasteuria* spp. | *Bacillus megaterium* |
| *Pasteuria* spp. | *Bacillus medusa* |
| *Pasteuria* spp. | *Bacillus metiens* |
| *Pasteuria* spp. | *Bacillus natto* |
| *Pasteuria* spp. | *Bacillus nigrificans* |
| *Pasteuria* spp. | *Bacillus papillae* |
| *Pasteuria* spp. | *Bacillus pumilus* |
| *Pasteuria* spp. | *Bacillus siamensis* |
| *Pasteuria* spp. | *Bacillus sphaericus* |
| *Pasteuria* spp. | *Bacillus subtilis* |
| *Pasteuria* spp. | *Bacillus thuringiensis* |
| *Pasteuria* spp. | *Bacillus uniflagellate* |

Further examples of specific combinations encompassed by the invention include, but are not limited to:

| Nematode-antagonistic biocontrol agent | Other agent(s) | Other agent(s) |
|---|---|---|
| *Pasteuria* spp. | clothianidin, imidacloprid and/or thiamethoxam | azoxystrobin |
| *Pasteuria* spp. | clothianidin, imidacloprid and/or thiamethoxam | cyproconazole |
| *Pasteuria* spp. | clothianidin, imidacloprid and/or thiamethoxam | difenoconazole |
| *Pasteuria* spp. | clothianidin, imidacloprid and/or thiamethoxam | fludioxonil |
| *Pasteuria* spp. | clothianidin, imidacloprid and/or thiamethoxam | mefenoxam and/or metalaxyl |
| *Pasteuria* spp. | clothianidin, imidacloprid and/or thiamethoxam | paclobutrazol |
| *Pasteuria* spp. | clothianidin, imidacloprid and/or thiamethoxam | prothioconazole |
| *Pasteuria* spp. | clothianidin and/or imidacloprid | sedaxane |
| *Pasteuria* spp. | thiamethoxam | sedaxane |
| *Pasteuria* spp. | clothianidin, imidacloprid and/or thiamethoxam | tebuconazole |
| *Pasteuria* spp. | clothianidin, imidacloprid and/or thiamethoxam | thiabendazole |
| *Pasteuria* spp. | clothianidin, imidacloprid and/or thiamethoxam | triticonazole |
| *Pasteuria* spp. | clothianidin, imidacloprid and/or thiamethoxam | thiamethoxam |
| *Pasteuria* spp. | clothianidin, imidacloprid and/or thiamethoxam | clothianidin |
| *Pasteuria* spp. | clothianidin, imidacloprid and/or thiamethoxam | cyantraniliprole |
| *Pasteuria* spp. | clothianidin, imidacloprid and/or thiamethoxam | diafenthiuron |
| *Pasteuria* spp. | clothianidin, imidacloprid and/or thiamethoxam | emamectin |
| *Pasteuria* spp. | clothianidin, imidacloprid and/or thiamethoxam | imidacloprid |
| *Pasteuria* spp. | clothianidin, imidacloprid and/or thiamethoxam | lambda-cyhalothrin |
| *Pasteuria* spp. | clothianidin, imidacloprid and/or thiamethoxam | lufenuron |
| *Pasteuria* spp. | clothianidin, imidacloprid and/or thiamethoxam | pirimicarb |
| *Pasteuria* spp. | clothianidin, imidacloprid and/or thiamethoxam | profenofos |
| *Pasteuria* spp. | clothianidin, imidacloprid and/or thiamethoxam | pymetrozine |
| *Pasteuria* spp. | clothianidin, imidacloprid and/or thiamethoxam | spinetoram |
| *Pasteuria* spp. | clothianidin, imidacloprid and/or thiamethoxam | spinosad |
| *Pasteuria* spp. | clothianidin, imidacloprid and/or thiamethoxam | spirotetramat |
| *Pasteuria* spp. | clothianidin, imidacloprid and/or thiamethoxam | tefluthrin |
| *Pasteuria* spp. | clothianidin, imidacloprid and/or thiamethoxam | thiodicarb |
| *Pasteuria* spp. | clothianidin and/or imidacloprid | abamectin |
| *Pasteuria* spp | thiamethoxam | abamectin |
| *Pasteuria* spp. | clothianidin, imidacloprid and/or thiamethoxam | fosthiazate |
| *Pasteuria* spp. | clothianidin, imidacloprid and/or thiamethoxam | *Bacillus* spp. |
| *Pasteuria* spp. | clothianidin, imidacloprid and/or thiamethoxam | trinexapac-ethyl |

In a preferred embodiment, the combination is in the form of a composition, which further comprises (III) one or more customary formulation auxiliaries. In a preferred embodiment, each combination is a composition that is in the form of a pre-mix formulated composition.

Combinations may demonstrate synergistic activity compared to the activity of the individual ingredients in the combination. There may be more than one agent, independently of each combination, from (II). The disclosure, therefore, makes available an improvement over the art.

Controlling, preventing or protecting and its inflections, within the context of the present invention, mean reducing any undesired effect, such as infestation or attack, and damage by a pest on a plant, part of the plant or plant propagation material to such a level that an improvement is demonstrated.

Each combination according to the invention may have advantageous properties for protecting plants against, for example, (i) pathogenic, such as phytopathogenic, especially fungi, attack or infestation, which result in disease and damage to the plant and/or (ii) insect or nematode attack or damage; particularly in the instance of plants, the present invention can control or prevent the pest damage on a seed, or parts of plant, plant organs and/or plants Further, a combination according to the invention, in the absence of pathogenic or insect and/or nematode pressure, may improve the growth of a plant.

Such properties are for example the synergistically enhanced actions of combinations compared to the individual ingredients of the combination (e.g. (I), and (II)), resulting in, for example, lower pathogenic pest damage, lower rates of application, or a longer duration of action. In the instance of agriculture, the enhanced actions may show an improvement in the growing characteristics of a plant by, for example, higher than expected control of the pest damage, or higher than expected yield, stand establishment, germination, etc.

The improvement in the growing (or growth) characteristics of a plant can manifest in a number of different ways, but will typically result in a better product of the plant. It can, for example, manifest in improving the yield and/or vigour of the plant or quality of the harvested product from the plant, which improvement may not be connected to the control of pests, such as fungi, insects and nematodes.

As used herein the phrase "improving the yield" of a plant relates to an increase in the yield of a product of the plant by a measurable amount over the yield of the same product of the plant produced under the same conditions, but without the application of the subject method. It is preferred that the yield be increased by at least about 0.5%, more preferred that the increase be at least about 1%, even more preferred is about 2%, and yet more preferred is about 4%, or more. Yield can be expressed in terms of an amount by weight or volume of a product of the plant on some basis. The basis can be expressed in terms of time, growing area, weight of plants produced, amount of a raw material used, or the like.

As used herein the phrase "improving the vigour" of a plant relates to an increase or improvement of the vigour rating, or the stand (the number of plants per unit of area), or the plant height, or the plant canopy, or the visual appearance (such as greener leaf colour), or the root rating, or emergence, or protein content, or increased tillering, or bigger leaf blade, or less dead basal leaves, or stronger tillers, or less fertilizer needed, or less seeds needed, or more productive tillers, or earlier flowering, or early grain maturity, or less plant verse (lodging), or increased shoot growth, or earlier germination, or any combination of these factors, or any other advantages familiar to a person skilled in the art, by a measurable or noticeable amount over the same factor of the plant produced under the same conditions, but without the application of the subject method.

When it is said that the present method is capable of "improving the yield and/or vigour" of a plant, the present method results in an increase in either the yield, as described above, or the vigor of the plant, as described above, or both the yield and the vigor of the plant.

In an embodiment, application to a plant, or propagation material thereof, a combination of nematode-antagonistic biocontrol agent and any one of thiamethoxam or cyantraniliprole provides improved yield and/or vigour. The application of the combination helps counter possible negative field conditions which expose plants to various stress factors, such as drought and floods Accordingly, the present disclosure also provides a method of improving the growing characteristics of a plant, which comprises applying to the plant, part of plant, and/or plant propagation material, the ingredients of the combination, as defined in the first aspect, in any desired sequence or simultaneously, especially in the absence of pathogenic or pests pressure.

Combinations of the disclosure can be used in the agricultural sector and related fields of use for controlling or preventing damage by pests, such as insect, nematode and pathogen.

Combinations according to the present disclosure, especially those containing (II) one or more pesticidal agents selected, independently from each other, from (B), (C), and (D), may be effective against pest control, such as control of pests selected from Nematoda, Insecta and Arachnida. In that instance, the combination can also be applied on the pest to control or prevent pest damage and protect the desired material (e.g. plant and part of plant) from pest damage.

Particular pests controlled by the compositions of the present technology include those from the class Nematoda, for example, the species of *Tylenchus* spp., *Atylenchus* spp., *Anguina* spp., *Rotylenchus* spp., *Criconema* spp., *Tylenchulus* spp., *Paratylenchus* spp., *Aphenlenchus* spp., *Bursaphelenchus* spp., *Paralongidorus* spp., *Trichodorus* spp., *Meloidogyne* spp. (for example, *Meloidogyne incoginita* and *Meloidogyne javanica*), *Heterodera* spp. (for example, *Heterodera glycines, Heterodera schachtii, Heterodora avenae* and *Heterodora trifolii*), *Globodera* spp. (for example, *Globodera rostochiensis*), *Radopholus* spp. (for example, *Radopholus similes*), *Rotylenchulus* spp., *Pratylenchus* spp. (for example, *Pratylenchus neglectans* and *Pratylenchus penetrans*), *Aphelenchoides* spp., *Helicotylenchus* spp., *Hoplolaimus* spp., *Paratrichodorus* spp., *Longidorus* spp., *Nacobbus* spp., *Subanguina* spp. *Belonolaimus* spp., *Criconemella* spp., *Criconemoides* spp. *Ditylenchus* spp., *Dolichodorus* spp., *Hemicriconemoides* spp., *Hemicycliophora* spp., *Hirschmaniella* spp., *Hypsoperine* spp., *Macroposthonia* spp., *Melinius* spp., *Punctodera* spp., *Quinisulcius* spp., *Scutellonema* spp., *Xiphinema* spp., and *Tylenchorhynchus* spp.

In the instance a combination contains (II) (F) Harpin, such a combination is also effective for improving the growth of a plant through, for example, activating the natural defence mechanism in the host plant, referred to as systemic acquired resistance (SAR) and/or nematode control, such as *Meloidogyne* spp. (for example, *Heterodera* spp. (for example, *Heterodera glycines, Heterodera schachtii, Heterodora avenae* and *Heterodora trifolii*).

Isoflavones are plant chemicals which occur largely in members of the Leguminosae plant family and two such examples are those defined in (II) (E). They are based on a simple diphenolic ring structure as described for example by Carlson et al (1980) Journal of Chromatography, 198, 193-197 and U.S. Pat. No. 7,033,621, the contents of which are incorporated by reference. Examples of isoflavones include, but are not limited to, genistein, biochanin A, formononetin, daidzein, glycitein, hesperetin, naringenin, chalcone, coumarin, Ambiol (2-methyl-4-[dimethylaminomethyl]-5-hydroxybenzimidazole), ascorbate and pratensein and the salts and esters thereof. The present invention contemplates the use of both naturally-occurring and synthetic isoflavone compounds.

In the instance a combination contains (II) one or more agents (E), such a combination is also effective for improving the growth of a plant through, for example, better availability of nutrients to the plant, such as water, and sulfates, nitrates, phosphates and metals, by improving the uptake by the roots.

The combinations according to the invention offers opportunities to manage resistance in pests, for example, *Plutella* spp. as well as to proactively manage insecticide resistance in various pests.

In the instance a combination contains (II) one or more agents (F) and/or (G), such a combination may also be effective for enhancing the plants' traits. Examples of enhanced plant traits include, but are not limited to, increased stem girth, change in leaf color, early flowering, synchronization in flowering, decrease in the lodging, control of the canopy size of a plant, delaying or eliminating tie-up of crops, increase in the disease resistance, enhancing the water utilization/improving the water use efficiency, including but not limited to decreasing the watering and/or less frequent watering (demonstrated by less wilting of the plant, the ability of the plant to rejuvenate following a suspension in watering), higher yield, higher quality/healthier plant appearance, greater transportability, decreasing the insect damage, and smaller plant canopies. Synchronized flowering is indicated by blooms materializing within 0.5 to 1 days of one another throughout the entire crop. Such a combination is particularly well suited for use for plants and propagation material thereof which are transplanted.

In an embodiment, further agent(s), such as active ingredient(s), can be used with each combination according to the present invention. Therefore, each of the combinations of the present invention may be mixed with, for example, one or more other known pesticides, such as other fungicides, insecticides, nematicides, etc. The use of additional agents, such as other active ingredients, can be for reasons, for example, broader spectrum control (e.g. wider variety of pests, diseases, etc), lower rates, synergy and economy. A skilled person would understand that a single pesticidal active ingredient may have activity in more than one area of pest control, for example, a pesticide may have fungicide, insecticide and nematicide activity. Specifically, aldicarb is known for insecticide, acaricide and nematicide activity, while metam is known for insecticide, herbicide, fungicide and nematicide activity, and thiabendazole and captan can provide nematicide and fungicide activity.

Combinations of the disclosure can be formulated for a particular use. Preferably, each combination is formulated for protecting cultivated plants or their propagation materials. Accordingly, each combination of the invention can be applied to the plant in a conventional manner, such as foliar spray. Advantageously, each of the combinations are formulated for plant propagation material, such as seed, treatment applications for improving the growth of a plant derived from the treated material (or seed), for example, by controlling or preventing damage by pests and/or pathogens, which are found in agriculture and forestry, and can particularly damage the plant in the early stages of its development.

Further, the present invention also envisages soil application of the combinations of the invention to control the soil-dwelling pests and/or soil-borne pathogens. Methods of applying to the soil can be via any suitable method, which ensures that the combination penetrates the soil, for example, nursery tray application, in furrow application, soil drenching, soil injection, drip irrigation, application through sprinklers or central pivot, incorporation into soil (broad cast or in band) are such methods.

The benefits from the invention can also be achieved either by (i) treating plant propagation material with a combination or (ii) applying to the locus where control is desired, generally the planting site, the combination, or both (i) and (ii). Indeed, the benefits from the invention can also be achieved by treating plant propagation material with one or more of the ingredients of the combination, and then applying to the locus where control is desired with the other ingredient(s) of the combination.

The term "plant propagation material" is understood to denote all the generative parts of the plant, such as seeds, which can be used for the multiplication of the latter and vegetative plant materials such as cuttings and tubers (for example, potatoes). Accordingly, as used herein, part of a plant includes propagation material. There may be mentioned, e.g., the seeds (in the strict sense), roots, fruits, tubers, bulbs, rhizomes, parts of plants. Germinated plants and young plants, which are to be transplanted after germination or after emergence from the soil, may also be mentioned. These young plants may be protected before transplantation by a total or partial treatment by immersion.

Parts of plant and plant organs that grow at later point in time are any sections of a plant that develop from a plant propagation material, such as a seed. Parts of plant, plant organs, and plants can also benefit from the pest damage protection achieved by the application of each combination on to the plant propagation material. In an embodiment, certain parts of a plant and certain plant organs that grow at later point in time can also be considered as plant propagation material, which can themselves be applied (or treated) with the combination; and consequently, the plant, further parts of the plant and further plant organs that develop from the treated parts of plant and treated plant organs can also benefit from the pest damage protection achieved by the application of each combinations on to the certain parts of plant and certain plant organs.

Methods for applying or treating pesticidal active ingredients and mixtures thereof on to plant propagation material, especially seeds, are known in the art, and include dressing, coating, pelleting and soaking application methods of the propagation material. Such methods are also applicable to the combinations according to the invention. In a preferred embodiment, the combination is applied or treated on to the plant propagation material by a method such that the germination is not induced; generally seed soaking induces germination because the moisture content of the resulting seed is too high. Accordingly, examples of suitable methods for applying (or treating) a plant propagation material, such as a seed, is seed dressing, seed coating or seed pelleting and alike.

It is preferred that the plant propagation material is a seed.

Although it is believed that the present method can be applied to a seed in any physiological state, it is preferred that the seed be in a sufficiently durable state that it incurs no damage during the treatment process. Typically, the seed would be a seed that had been harvested from the field; removed from the plant; and separated from any cob, stalk, outer husk, and surrounding pulp or other non-seed plant material. The seed would preferably also be biologically stable to the extent that the treatment would cause no biological damage to the seed. It is believed that the treatment can be applied to the seed at any time between harvest of the seed and sowing of the seed or during the sowing process (seed directed applications). The seed may also be primed either before or after the treatment.

Even distribution of the ingredients in the combination and adherence thereof to the seeds is desired during propagation material treatment. Treatment could vary from a thin film (dressing) of the formulation containing the combination, for example, a mixture of active ingredient(s), on a plant propagation material, such as a seed, where the original size and/or shape are recognizable to an intermediary state (such as a coating) and then to a thicker film (such as pelleting with many layers of different materials (such as carriers, for example, clays; different formulations, such as of other active ingredients; polymers; and colourants) where the original shape and/or size of the seed is no longer recognisable.

An aspect of the present invention includes application of the combinations onto the plant propagation material in a targeted fashion, including positioning the ingredients in the combination onto the entire plant propagation material or on only parts thereof, including on only a single side or a portion of a single side. One of ordinary skill in the art would understand these application methods from the description provided in EP954213B1 and WO06/112700.

The combinations described herein can also be used to enhance the growth of a plant through treating, or applying, a combination according to the present on to a "pill" or a suitable substrate and placing, or sowing, the treated pill, or substrate, next to a plant propagation material. Such techniques are known in the art, particularly in EP1124414, WO07/67042, and WO07/67044.

Application of the combinations described herein onto plant propagation material also includes protecting the plant propagation material treated with the combination of the present invention by placing one or more pesticide-containing particles next to a pesticide-treated seed, wherein the amount of pesticide is such that the pesticide-treated seed and the pesticide-containing particles together contain an Effective Dose of the pesticide and the pesticide dose contained in the pesticide-treated seed is less than or equal to the Maximal Non-Phytotoxic Dose of the pesticide. Such techniques are known in the art, particularly in WO2005/120226.

Application of the combinations onto the seed also includes controlled release coatings on the seeds, wherein the ingredients of the combinations are incorporated into materials that release the ingredients over time. Examples of controlled release seed treatment technologies are generally known in the art and include polymer films, waxes, or other seed coatings, wherein the ingredients may be incorporated into the controlled release material or applied between layers of materials, or both.

Seed can be treated by applying thereto the insecticidal compound (I) and at least one agent (II) in any desired sequence or simultaneously.

The seed treatment occurs to an unsown seed, and the term "unsown seed" is meant to include seed at any period between the harvest of the seed and the sowing of the seed in the ground for the purpose of germination and growth of the plant.

Treatment to an unsown seed is not meant to include those practices in which the active ingredient is applied to the soil but would include any application practice that would target the seed during the planting process.

Preferably, the treatment occurs before sowing of the seed so that the sown seed has been pre-treated with the combination. In particular, seed coating or seed pelleting are preferred in the treatment of the combinations according to the invention. As a result of the treatment, the ingredients in each combination are adhered on to the seed and therefore available for pest control.

The treated seeds can be stored, handled, sowed and tilled in the same manner as any other active ingredient treated seed.

Each combination according to the present invention is suitable for plants of the crops: cereals, such as wheat, barley, rye, oats, rice or sorghum; maize (fodder maize and sugar maize/sweet and field corn); beet, such as sugar or fodder beet; fruit, for example pomaceous fruit, stone fruit, tree nut or soft fruit, such as apples, pears, plums, peaches, bananas, almonds, walnuts, pistachios, cherries or berries, for example strawberries, raspberries or blackberries; leguminous crops, such as beans, lentils, peas or soya; oil crops, such as oilseed rape, mustard, poppies, olives, sunflowers, coconut, castor, cocoa or ground nuts; cucurbits, such as pumpkins, marrow, cucumbers or melons; fibre plants, such as cotton, flax, hemp or jute; citrus fruit, such as oranges, lemons, grapefruit or tangerines; vegetables, such as spinach, lettuce, asparagus, cabbages, iceberg, carrots, onions, tomatoes, paprika, potatoes or bell peppers; Lauraceae, such as avocado, Cinnamonium or camphor; and also tobacco, nuts, coffee, eggplants, sugarcane, tea, pepper, grapevines, hops, the plantain family including bananas, latex plants, lawn, turf, fodder grass, and ornamentals, such as petunias, geranium/pelargoniums, pansies and impatiens; and shrubs, broad-leaved trees and evergreens, such as conifers. In particular, the combination is suitable for coffee, citrus, stone fruits (especially apple, pears, plums, peaches), tree nuts (especially almonds and pistachios), and vegetable crops. In particular, cotton, soya, cereals, maize, vegetables, and bananas.

Each of the combinations according to the present invention are particularly suitable for use in maize, cereals (including rice), oil seed rape/canola, soybean, cotton, sugar beet, sunflower, potato, beans, sorghum, peas, peanuts, bananas, as well as vegetables such as cale crops, and fruiting vegetables.

The term "crops" is to be understood as including also crop plants which have been so transformed by the use of recombinant DNA techniques that they are capable of synthesising one or more selectively acting toxins, such as are known, for example, from toxin-producing bacteria, especially those of the genus *Bacillus*.

Toxins that can be expressed by such transgenic plants include, for example, insecticidal proteins from *Bacillus cereus* or *Bacillus popilliae*; or insecticidal proteins from *Bacillus thuringiensis*, such as δ-endotoxins, e.g. Cry1Ab, Cry1Ac, Cry1F, Cry1Fa2, Cry2Ab, Cry3A, Cry3Bb1 or Cry9C, or vegetative insecticidal proteins (Vip), e.g. Vip1, Vip2, Vip3 or Vip3A; or insecticidal proteins of bacteria colonising nematodes, for example *Photorhabdus* spp. or *Xenorhabdus* spp., such as *Photorhabdus luminescens, Xenorhabdus nematophilus;* toxins produced by animals, such as scorpion toxins, arachnid toxins, wasp toxins and other insect-specific neurotoxins; toxins produced by fungi, such as *Streptomycetes* toxins, plant lectins, such as pea lectins, barley lectins or snowdrop lectins; agglutinins; proteinase inhibitors, such as trypsin inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyltransferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

In the context of the present invention there are to be understood by δ-endotoxins, for example Cry1Ab, Cry1Ac, Cry1F, Cry1Fa2, Cry2Ab, Cry3A, Cry3Bb1 or Cry9C, or vegetative insecticidal proteins (Vip), for example Vip1, Vip2, Vip3 or Vip3A, expressly also hybrid toxins, truncated toxins and modified toxins. Hybrid toxins are produced recombinantly by a new combination of different domains of those proteins (see, for example, WO 02/15701). Truncated toxins, for example a truncated Cry1Ab, are known. In the case of modified toxins, one or more amino acids of the naturally occurring toxin are replaced. In such amino acid replacements, preferably non-naturally present protease recognition sequences are inserted into the toxin, such as, for example, in the case of Cry3A055, a cathepsin-G-recognition sequence is inserted into a Cry3A toxin (see WO 03/018810).

Examples of such toxins or transgenic plants capable of synthesising such toxins are disclosed, for example, in EP0374753A, WO 93/07278, WO 95/34656, EP0427529A, EP451878A and WO 03/052073.

The processes for the preparation of such transgenic plants are generally known to the person skilled in the art and are described, for example, in the publications mentioned above. CryI-type deoxyribonucleic acids and their preparation are known, for example, from WO 95/34656, EP0367474A, EP0401979A and WO 90/13651.

The toxin contained in the transgenic plants imparts to the plants tolerance to harmful insects. Such insects can occur in any taxonomic group of insects, but are especially commonly found in the beetles (Coleoptera), two-winged insects (Diptera) and butterflies (Lepidoptera).

Transgenic plants containing one or more genes that code for an insecticidal resistance and express one or more toxins are known and some of them are commercially available. Examples of such plants are: YieldGard® (maize variety that expresses a Cry1Ab toxin); YieldGard Rootworm® (maize variety that expresses a Cry3Bb 1 toxin); YieldGard Plus® (maize variety that expresses a Cry1Ab and a Cry3Bb1 toxin); Starlink® (maize variety that expresses a Cry9C toxin); Herculex I® (maize variety that expresses a Cry1Fa2 toxin and the enzyme phosphinothricine N-acetyltransferase (PAT) to achieve tolerance to the herbicide glufosinate ammonium); NuCOTN 33B® (cotton variety that expresses a Cry1Ac toxin); Bollgard I® (cotton variety that expresses a Cry1Ac toxin); Bollgard II® (cotton variety that expresses a Cry1Ac and a Cry2Ab toxin); VipCot® (cotton variety that expresses a Vip3A and a Cry1Ab toxin); NewLeaf® (potato variety that expresses a Cry3A toxin); NatureGard®, Agrisure® GT Advantage (GA21 glyphosate-tolerant trait), Agrisure® CB Advantage (Bt11 corn borer (CB) trait) and Protecta®.

Further examples of such transgenic crops are:
1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated Cry1Ab toxin. Bt11 maize also transgenically expresses the enzyme PAT to achieve tolerance to the herbicide glufosinate ammonium.
2. Bt176 Maize from Syngenta Seeds SAS, Chemin de l'Hobit 27, F-31 790 St. Sauveur, France, registration number C/FR/96/05/10. Genetically modified Zea mays which has been rendered resistant to attack by the European corn borer (*Ostrinia nubilalis* and *Sesamia nonagrioides*) by transgenic expression of a Cry1Ab toxin. Bt176 maize also transgenically expresses the enzyme PAT to achieve tolerance to the herbicide glufosinate ammonium.
3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified Cry3A toxin. This toxin is Cry3A055 modified by insertion of a cathepsin-G-protease recognition sequence. The preparation of such transgenic maize plants is described in WO 03/018810.
4. MON 863 Maize from Monsanto Europe S.A. 270-272 Avenue de Tervuren, B-1150 Brussels, Belgium, registration number C/DE/02/9. MON 863 expresses a Cry3Bb1 toxin and has resistance to certain Coleoptera insects.
5. IPC 531 Cotton from Monsanto Europe S.A. 270-272 Avenue de Tervuren, B-1150 Brussels, Belgium, registration number C/ES/96/02.
6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain Lepidoptera insects and of the PAT protein for achieving tolerance to the herbicide glufosinate ammonium.
7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603× MON 810 Maize transgenically expresses the protein CP4 EPSPS, obtained from *Agrobacterium* sp. strain CP4, which imparts tolerance to the herbicide Roundup® (contains glyphosate), and also a Cry1Ab toxin obtained from *Bacillus thuringiensis* subsp. kurstaki which brings about tolerance to certain Lepidoptera, include the European corn borer.

The mass ratio of any two ingredients in each combination is selected as to give the desired, for example, synergistic action. In general, the mass ratio would vary depending on the specific ingredient and how many ingredients are present in the combination. Generally, the mass ratio between any two ingredients in any combination of the present invention, independently of one another, is from 100:0.1 to 0.1:100 including from 100:1 to 1:100, 99:1, 98:2, 97:3, 96:4, 95:5, 94:6, 93:7, 92:8, 91:9, 90:10, 89:11, 88:12, 87:13, 86:14, 85:15, 84:16, 83:17, 82:18, 81:19, 80:20, 79:21, 78:22, 77:23, 76:24, 75:25, 74:26, 73:27, 72:28, 71:29, 70:30, 69:31, 68:32, 67:33, 66:34, 65:45, 64:46, 63:47, 62:48, 61:49, 60:40, 59:41, 58:42, 57:43, 56:44, 55:45, 54:46, 53:47, 52:48, 51:49, 50:50, 49:51, 48:52, 47:53, 46:54, 45:55, 44:56, 43:57, 42:58, 41:59, 40:60, 39:61, 38:62, 37:63, 36:64, 35:65, 34:66, 33:67, 32:68, 31:69, 30:70, 29:71, 28:72, 27:73, 26:74, 25:75, 24:76, 23:77, 22:78, 21:79, 20:80, 19:81, 18:82, 17:83, 16:84, 15:85, 14:86, 13:87, 12:88, 11:89, 10:90, 9:91, 8:92, 7:93, 6:94, 5:95, 4:96, 3:97, 2:98, to 1:99. Preferred mass ratios between any two components of present invention are from 75:1 to 1:75, more preferably, 50:1 to 1.50, especially 25:1 to 1:25, advantageously 10:1 to 1:10, such as 5:1 to 1:5.

In an embodiment, the ratio of (I) to (II), wherein (II) is one or more of (A), is 1:10 to 500:1, such as 1:7 to 400:1, preferably 10:1 to 300:1, such as 15:1 to 80:1, preferably 20:1 to 50:1.

In an embodiment, the ratio of (I) to (II), wherein (II) is one or more of (B), is likely to 1:10 to 10:1, such as 1:5 to 5:1, preferably 1:3 to 3:1.

In an embodiment, the ratio of (I) to (II), wherein (II) is (F) harpin, is 1000:1 to 5:1, such as 300:1 to 30:1, preferably 100:1 to 40:1.

In an embodiment, the ratio of (I) to (II), wherein (II) is (D) the specific Bacillus firmus strain, is 15:1 to 1:3, such as 10:1 to 1:5, preferably 3:1 to 1:1.

In an embodiment, the ratio of (I) to (II), wherein (II) is Formononetin, is 5:1 to 1:5, such as 1:1 to 10:1, preferably 3:1 to 5:1.

In an embodiment, the ratio of (I) to (II), wherein (II) is Genistein, is 1:1000 to 1:150,000, such as 1:10000 to 1:100000, preferably 1:50000 to 1:80000.

In an embodiment, the ratio of (I) to (II), wherein (II) is a plant growth regulator, is 1:10 to 10:1, such as 1:5 to 5:1, preferably 1:3 to 3:1.

In an embodiment, the ratio of (I) to (II), wherein (II) is a plant activator, is 1:10 to 10:1, such as 1:5 to 5:1, preferably 1:3 to 3:1.

In an embodiment, in the instance (II) is thiamethoxam, the ratio of (I) to (II), is 1:5 to 5:1, such as 2 to 5:1.

The rates of application (use) of a combination vary, for example, according to type of use, type of crop, the specific agent (II) in the combination, type of plant propagation material (if appropriate), but is such that the active ingredients in the combination is an effective amount to provide the desired enhanced action (such as disease or pest control) and can be determined by trials and routine experimentation known to one of ordinary skill in the art. Generally for foliar or soil treatments, application rates can vary from 0.05 to 3 kg per hectare (g/ha) of ingredients.

Generally for seed treatments, application rates can vary from 0.5 to 1000 g/100 kg of seeds of ingredients. In an embodiment, compound (I) is applied at a rate of 0.01 to 2, preferably 0.03 to 1.5, mg ai/seed, depending on the crop. Whereas the rates of application of the agents indicated in (A), (B), (C), (D) and (E) can vary depending on the specific agent and type of crop. Such rates would be readily available to a skilled person.

The methods according to the invention for controlling pests of the abovementioned type is carried out in a manner known per se to those skilled in the art, depending on the intended aims and prevailing circumstances, that is to say by spraying, wetting, atomizing, dusting, brushing on, seed dressing, scattering or pouring of the composition. In the case of spore forming bacteria and fungi, the application rates with respect to plant propagation material (e.g. seed treatment) preferably range from about $1 \times 10^5$ to $1 \times 10^{12}$ (or more) spores/seeds. Preferably, the spore concentration is about $1 \times 10^6$ to about $1 \times 10^{11}$ spores/seed. Similar application rates may also be used for agents indicated in (D). For example, Bacillus species may be present in the range of about $1 \times 10^5$ to $1 \times 10^{12}$ (or more) colony forming units CFU)/seeds. In another example, the cell concentration is in the range of about $1 \times 10^6$ to about $1 \times 10^{11}$ CFU/seed.

The plant propagation material treated by each combination of the present disclosure may be, therefore, resistant to pest damage; accordingly, the present invention also provides a pest resistant plant propagation material which is treated with each combination and consequently at least the ingredients thereof are adhered on the propagation material, such as seed.

The seed treatment combinations and compositions can also comprise or may be applied together and/or sequentially with further active compounds. These further useful active compounds can be fertilizers or micronutrient donors (such as Mo, Zn and/or Co) or other preparations that influence plant growth, such as inoculants (e.g. a strain of nitrogen-fixing bacteria), plant inducers (e.g. nod factors such as disclosed in US2005187107).

In a preferred embodiment of the invention, soybean seeds and transgenic soybean seeds are treated with a combination of the present invention. In addition, the soybean seeds may be inoculated with an appropriate strain of nitrogen-fixing bacteria for the purpose of promoting plant growth. Preferably, seeds may be inoculated with an effective bacterial strain such as *Rhizobium* spp. or *Azospirillium* spp. before sowing. The primary effect of such bacteria is in the fixation of atmospheric nitrogen into a useable form for the plant. Rhizobia bacteria, for example, is especially preferred in order to form nodules on the plant roots that are sustained by the plant and in turn provide nitrogen for the plant as mentioned above.

In a further embodiment, a soybean plant propagation material is treated with a plant inducer, e.g. a nod factor derived from *Bradyrhizobium japonicum, Sinorhizobium Sinorhizobium meliloti, Bradyrhizobium* sp. (Arachis), or *Rhizobium leguminosarum* biovar *phaseoli*, viceae, or *trifolii*.

In an aspect, the present invention also envisages use of the combinations of the present invention with glyphospate tolerant plants, especially glyphospate tolerant soybean plants, in particular for the control of asian soybean rust. Accordingly, the present invention provides a method comprising (α) applying a combination according to the invention as defined in the first aspect, especially those containing (II) one or more pesticidal agents (A), to a glyphosate tolerant plant propagation material, preferably soybean propagation material, and (β) applying a pesticidal composition (B) to the resulting plant, part of plant and/or the locus thereof one or more times (i) before emergence, (ii) after emergence, or (iii) both (i) and (ii), provided that pesticide composition (B) comprises glyphosate.

Generally, glyphosate-containing composition can be applied, if applied only once, at a rate of 960 g ai/ha; if applied twice the rate can vary from 1200 to 1680 g ai/ha. The rates and number of applications vary according to the particular conditions. Preferably, the composition (B) is applied three times with an application rate of 960, 720 and 400 g ai/ha respectively. In such an embodiment, the present invention controls, prevents or treats *Phakopsora pachyrhizi* and/or *P. meibomiae*, especially *Phakopsora pachyrhizi*.

Each of the combinations of the present invention may also comprise alkali metal, alkaline earth metal, metal, or ammonium salts. Zinc chloride and alkali metal, alkaline earth metal, or ammonium salts of mineral acids, especially nitrates, phosphates, sulfates, chlorides, and carbonates of sodium, potassium, ammonium, magnesium, and calcium are preferred.

Depending upon the particular plant propagation material to be treated, the conditions under which it is to be stored, and the soil and weather conditions under which it is expected to germinate and grow, the combinations of the present invention may include a wide spectrum of one or more additives. Such additives include, but are not limited to, uv-protectants, pigments, dyes, extenders such as flour, dispersing agents, excipients, anti-freezing agents, preservatives, herbicidal safeners, seed safeners, seed conditioners, micronutients, fertilizers, biocontrol agents, surfactants, sequestering agents, plasticizers, colorants, brighteners, emulsifiers, flow agents such as calcium stearate, talc and vermiculite, coalescing agents, defoaming agents, humectants, thickeners, waxes, bactericides, insecticides, pesticides, and fillers such as cellulose, glass fibers, clay, kaolin, talc, pulverized tree bark (e.g., Douglas fir bark or alderbark), calcium carbonate and wood meal, and odor-modifying agents. Typical excipients include finely divided mineral substances such as pumice, attapulgite, bentonite, kaoline zeolite, diatomite, and other clays, modified diatomaceous adsorbents, charcoal, vermiculite, finely divided organic substances such as peat moss, wood powder, and the like. Such additives are commercially available and known in the art.

The insecticidal compound (I) and one or more agents (II), and optionally any other pesticides, may be used either in pure form, i.e., as a solid active ingredient, for example, in a specific particle size, or preferably together with at least one of the auxiliary (also known as adjuvants) customary in formulation technology, such as extenders, e.g., solvents or solid carriers, or surface-active compounds (surfactants), in the form of a formulation, in the present invention. Generally, the insecticidal compound (I) and one or more agents (II) are in the form of a formulation composition with one or more of customary formulation auxiliaries.

Therefore, each combination of the insecticidal compound (I) and one or more agents (II) is normally used in the form of formulations. The ingredients in the combination can be applied to the locus where control is desired either simultaneously or in succession at short interval, for example on the same day, if desired together with further carriers, surfactants or other application-promoting adjuvants customarily employed in formulation technology. In a preferred embodiment, the ingredients in the combination are applied simultaneously.

In the event ingredients of the combinations are applied simultaneously in the present invention, they may be applied as a composition containing the combination, in which case each of (I) and (II) can be obtained from a separate formulation source and mixed together (known as a tank-mix, ready-to-apply, spray broth, or slurry), optionally with other pesticides, or (I) and (II) can be obtained as single formulation mixture source (known as a pre-mix, concentrate, formulated product), and optionally mixed together with other pesticides.

In an embodiment, each combination of the present invention is applied as a composition. Accordingly, the present invention includes a composition comprising (I) and (II), and optionally other pesticides, and optionally one or more customary formulation auxiliaries; which may be in the form of a tank-mix or pre-mix composition.

In an embodiment, each combination of (I) and (II) with one or more customary formulation auxiliaries is provided in the form of a pre-mix composition (or formulated product).

Alternative to the actual synergistic action with respect to pesticidal activity, the combinations according to the invention also can have surprising advantageous properties which can also be described, in a wider sense, as synergistic activity. Examples of such advantageous properties that may be mentioned are: advantageous behaviour during formulation and/or upon application, for example upon grinding, sieving, emulsifying, dissolving or dispensing; increased storage stability; improved stability to light; more advantageous degradability; improved toxicological and/or ecotoxicological behaviour; or any other advantages familiar to a person skilled in the art.

Examples of foliar formulation types for pre-mix compositions are:
GR: Granules
WP: wettable powders
WG: water dispersable granules (powders)
SG: water soluble granules
SL: soluble concentrates
EC: emulsifiable concentrate
EW: emulsions, oil in water
ME: micro-emulsion
SC: aqueous suspension concentrate
CS: aqueous capsule suspension OD: oil-based suspension concentrate, and
SE: aqueous suspo-emulsion.

Whereas, examples of seed treatment formulation types for pre-mix compositions are:
WS: wettable powders for seed treatment slurry
LS: solution for seed treatment
ES: emulsions for seed treatment
FS: suspension concentrate for seed treatment
WG: water dispersible granules, and
CS: aqueous capsule suspension.

Examples of formulation types suitable for tank-mix compositions are solutions, dilute emulsions, suspensions, or a mixture thereof, and dusts.

As with the nature of the formulations, the methods of application, such as foliar, drench, spraying, atomizing, dusting, scattering, coating or pouring, are chosen in accordance with the intended objectives and the prevailing circumstances.

The tank-mix compositions are generally prepared by diluting with a solvent (for example, water) the one or more pre-mix compositions containing different pesticides, and optionally further auxiliaries.

Suitable carriers and adjuvants can be solid or liquid and are the substances ordinarily employed in formulation technology, e.g. natural or regenerated mineral substances, solvents, dispersants, wetting agents, tackifiers, thickeners, binders or fertilizers.

The formulations are prepared in known manner, e.g., by homogeneously mixing and/or grinding the active ingredients with extenders, e.g., solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates, such as dibutyl phthalate or dioctyl phthalate, aliphatic hydrocarbons, such as cyclohexane or paraffins, alcohols and glycols and their ethers and esters, such as ethanol, ethylene glycol, ethylene glycol monomethyl or monoethyl ether, ketones, such as cyclohexanone, strongly polar solvents, such as N-methyl-2-pyrrolidone, dimethyl sulfoxide or dimethylformamide, as well as vegetable oils or epoxidised vegetable oils, such as epoxidised coconut oil or soybean oil; or water.

The solid carriers used, e.g., for dusts and dispersible powders, are normally natural mineral fillers, such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite, and suitable nonsorbent carriers are, for example, calcite or sand. In addition, a great number of pregranulated materials of inorganic or organic nature can be used, e.g., especially dolomite or pulverized plant residues.

Depending upon the nature of the ingredients to be formulated, suitable surface-active compounds are non-ionic, cationic and/or anionic surfactants having good emulsifying, dispersing and wetting properties. The term "surfactants" will also be understood as comprising mixtures of surfactants.

Particularly advantageous application-promoting adjuvants are also natural or synthetic phospholipids of the cephalin and lecithin series, e.g., phosphatidylethanolamine, phosphatidylserine, phosphatidylglycerol and lysolecithin.

Generally, a tank-mix formulation for foliar or soil application comprises 0.1 to 20%, especially 0.1 to 15%, of the desired ingredients, and 99.9 to 80%, especially 99.9 to 85%, of a solid or liquid auxiliaries (including, for example, a solvent such as water), where the auxiliaries can be a surfactant in an amount of 0 to 20%, especially 0.1 to 15%, based on the tank-mix formulation.

Typically, a pre-mix formulation for foliar application comprises 0.1 to 99.9%, especially 1 to 95%, of the desired ingredients, and 99.9 to 0.1%, especially 99 to 5%, of a solid or liquid adjuvant (including, for example, a solvent such as water), where the auxiliaries can be a surfactant in an amount of 0 to 50%, especially 0.5 to 40%, based on the pre-mix formulation.

Normally, a tank-mix formulation for seed treatment application comprises 0.25 to 80%, especially 1 to 75%, of the desired ingredients, and 99.75 to 20%, especially 99 to 25%, of a solid or liquid auxiliaries (including, for example, a solvent such as water), where the auxiliaries can be a surfactant in an amount of 0 to 40%, especially 0.5 to 30%, based on the tank-mix formulation.

Typically, a pre-mix formulation for seed treatment application comprises 0.5 to 99.9%, especially 1 to 95%, of the desired ingredients, and 99.5 to 0.1%, especially 99 to 5%, of a solid or liquid adjuvant (including, for example, a solvent such as water), where the auxiliaries can be a surfactant in an amount of 0 to 50%, especially 0.5 to 40%, based on the pre-mix formulation.

Whereas commercial products will preferably be formulated as concentrates (e.g., pre-mix composition (formulation)), the end user will normally employ dilute formulations (e.g., tank mix composition).

Preferred seed treatment pre-mix formulations are aqueous suspension concentrates. The formulation can be applied to the seeds using conventional treating techniques and machines, such as fluidized bed techniques, the roller mill method, rotostatic seed treaters, and drum coaters. Other methods, such as spouted beds may also be useful. The seeds may be presized before coating. After coating, the seeds are typically dried and then transferred to a sizing machine for sizing. Such procedures are known in the art.

In general, the pre-mix compositions of the invention contain 0.5 to 99.9 especially 1 to 95, advantageously 1 to 50 , %, by mass of the desired ingredients, and 99.5 to 0.1, especially 99 to 5, %, by mass of a solid or liquid adjuvant (including, for example, a solvent such as water), where the auxiliaries (or adjuvant) can be a surfactant in an amount of 0 to 50, especially 0.5 to 40, %, by mass based on the mass of the pre-mix formulation.

A preferred embodiment is a plant propagation material treating (or protecting) composition, wherein said plant propagation material protecting composition comprises additionally a colouring agent. The plant propagation material protecting composition or mixture may also comprise at least one polymer from water-soluble and water-dispersible film-forming polymers that improve the adherence of the active ingredients to the treated plant propagation material, which polymer generally has an average molecular weight of at least 10,000 to about 100,000.

The Examples which follow serve to illustrate the various aspects of the disclosure.

Formulation Examples

| Wettable powders | a) | b) | c) |
|---|---|---|---|
| active ingredients | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| phenol polyethylene glycol ether (7-8 mol of ethylene oxide) | — | 2% | — |

-continued

| Wettable powders | a) | b) | c) |
|---|---|---|---|
| highly dispersed silicic acid | 5% | 10% | 10% |
| Kaolin | 62% | 27% | — |

The combination is thoroughly mixed with the adjuvants and the mixture is thoroughly ground in a suitable mill, affording wettable powders that can be diluted with water to give suspensions of the desired concentration.

| Powders for dry seed treatment | a) | b) | c) |
|---|---|---|---|
| active ingredients | 25% | 50% | 75% |
| light mineral oil | 5% | 5% | 5% |
| highly dispersed silicic acid | 5% | 5% | — |
| Kaolin | 65% | 40% | — |
| Talcum | — | — | 20 |

The combination is thoroughly mixed with the adjuvants and the mixture is thoroughly ground in a suitable mill, affording powders that can be used directly for seed treatment.

| Emulsifiable concentrate | |
|---|---|
| active ingredients | 10% |
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |
| Cyclohexanone | 30% |
| xylene mixture | 50% |

Emulsions of any required dilution, which can be used in plant protection, can be obtained from this concentrate by dilution with water.

| Dusts | a) | b) | c) |
|---|---|---|---|
| Active ingredients | 5% | 6% | 4% |
| Talcum | 95% | — | — |
| Kaolin | — | 94% | — |
| mineral filler | — | — | 96% |

Ready-for-use dusts are obtained by mixing the combination with the carrier and grinding the mixture in a suitable mill. Such powders can also be used for seed dry dressings.

| Extruder granules | |
|---|---|
| Active ingredients | 15% |
| sodium lignosulfonate | 2% |
| carboxymethylcellulose | 1% |
| Kaolin | 82% |

The combination is mixed and ground with the adjuvants, and the mixture is moistened with water. The mixture is extruded and then dried in a stream of air.

| Coated granules | |
|---|---|
| Active ingredients | 8% |
| polyethylene glycol (mol. wt. 200) | 3% |
| Kaolin | 89% |

The finely ground combination is uniformly applied, in a mixer, to the kaolin moistened with polyethylene glycol. Non-dusty coated granules are obtained in this manner.

| Suspension concentrate | |
|---|---|
| active ingredients | 40% |
| propylene glycol | 10% |
| nonylphenol polyethylene glycol ether (15 mol of ethylene oxide) | 6% |
| Sodium lignosulfonate | 10% |
| carboxymethylcellulose | 1% |
| silicone oil (in the form of a 75 % emulsion in water) | 1% |
| Water | 32% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

| Flowable concentrate for seed treatment | |
|---|---|
| active ingredients | 40% |
| propylene glycol | 5% |
| copolymer butanol PO/EO | 2% |
| Tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Slow Release Capsule Suspension 28 parts of the combination are mixed with 2 parts of an aromatic solvent and 7 parts of toluene diisocyanate/polymethylene-polyphenylisocyanate-mixture (8:1). This mixture is emulsified in a mixture of 1.2 parts of polyvinylalcohol, 0.05 parts of a defoamer and 51.6 parts of water until the desired particle size is achieved. To this emulsion a mixture of 2.8 parts 1,6-diaminohexane in 5.3 parts of water is added. The mixture is agitated until the polymerization reaction is completed. The obtained capsule suspension is stabilized by adding 0.25 parts of a thickener and 3 parts of a dispersing agent. The capsule suspension formulation contains 28% of the active ingredients. The medium capsule diameter is 8-15 microns. The resulting formulation is applied to seeds as an aqueous suspension in an apparatus suitable for that purpose.

Using such formulations, either straight or diluted, plant propagation material can be treated and protected against pest damage, for example, from pathogen(s), by, for example, spraying, pouring or immersing.

The combinations according to the invention are distinguished by the fact that they are especially well tolerated by plants and are environmentally friendly.

Combination Examples

A plug measuring 0.75 inch (approximately 1.9 cm) in diameter and 1 inch (approx. 2.5 cm) in depth was removed from each 3 inch diameter×8 inch deep (approx. 7.6×20 cm) plastic pot. Five thousand Heterodera glycines race 3 eggs were placed at the bottom of the plug hole. A soybean variety 3.6-B6 seed was placed on top of the inoculum. Six replicates were made for each treatment group. In addition to untreated control, the treatment groups were *Pasteuria nishizawae*, *Bacillus firmus*, and *Pasteuria nishizawae+Bacillus firmus*.

*Bacillus firmus* came applied as a seed treatment (available commercially, for example, from Bayer Crop Science as VOTIVO product, PONCHO/VOTIVO, having *Bacillus firmus* concentration at least $2\times10^9$ cfu/ml+clothianidin (0.13 mg/seed)). A point application containing *Pasteuria nishizawae* (approximately $5.0\times10^9$ spores) was applied directly to the seed in the pot. The plug was replaced in the hole to cover the seed. The soil was Vero Beach (Florida, USA) top soil, pH 5.9 (approximate composition sand 93%, silt 2%, clay 2%, organic matter 3%).

At 28 days after planting, plant height was measured and plants were removed from the pots. Soil was gently rinsed from the roots. The rinsed roots were placed in a 20 mesh over a 60 mesh sieve. The root system was blasted with water to remove cyst nematode females. The 20 mesh sieve was removed and the cysts were washed to the bottom of the 60 mesh sieve. The cysts were rinsed into a tube for counting under a stereoscope. Later the dry root weights were measured.

This example illustrates a combination example according to one embodiment of the disclosure. Results were as follows:

| | Averaged data points for all replicates | | |
|---|---|---|---|
| Treatment Component(s) | Height (cm) | Cyst Count | Root Weight (g) |
| Untreated Control | 14.3 | 375 | 0.183 |
| *Pasteuria nishizawae* | 13.5 | 366 | 0.245 |
| *Bacillus firmus* | 13.7 | 304 | 0.168 |
| *Pasteuria nishizawae* + *Bacillus firmus* | 12.5 | 81 | 0.164 |

Looking closer at the cyst count as an indicator of nematode control, the data show:

| Treatment Components | Average Cyst Count | % Control Observed | Colby Expected Control |
|---|---|---|---|
| Untreated Control | 375 | 0.00 | — |
| *Pasteuria nishizawae* | 366 | 2.40 | — |
| *Bacillus firmus* | 304 | 18.93 | — |
| *Pasteuria nishizawae* + *Bacillus firmus* | 81 | 78.40 | 20.88 |

As illustrated, the expected control for the *Pasteuria* species+*Bacillus* species combination was 20.88%, however, 78.40% control was observed evidencing a strong synergistic effect of the combination.

In a preferred embodiment, each of the combinations of the present invention is a plant propagation material, preferably seed, treating composition.

In each aspect and embodiment of the invention, "consisting essentially" and inflections thereof are a preferred embodiment of "comprising" and its inflections, and "consisting of" and inflections thereof are a preferred embodiment of "consisting essentially of" and its inflections.

Use of a term in a singular form encompasses that term in plural form and vice a versa.

We claim:

1. A method of protecting a plant propagation material, a plant, a part of a plant and/or a plant organ that subsequently grows against pest damage, the method comprising:
applying to the plant propagation material, which is a seed, a combination comprising
(I) *Pasteuria nishizawae* applied to the seed at a rate in the range of $1\times10^5$ to $1\times10^{12}$ spores/seed and
(II) *Bacillus firmus* applied to the seed at a rate in the range of $1\times10^5$ to $1\times10^{12}$ CFU/seed in any desired sequence or simultaneously.

2. The method according to claim 1, further comprising applying to the plant propagation material at least one fungicide selected from the group consisting of amisulbrom, azoxystrobin, boscalid, captan, carboxin, cyproconazole, cyprodinil, difenoconazole, dimoxystrobin, enestrobin, fludioxonil, fluopyram, fluoxastrobin, fluquinconazole, flutriafol, fuberidazole, flutriafol, fluxapyroxad, ipconazole, mancozeb, mefenoxam, metalaxyl, myclobutanil, penflufen, penthiopyrad, prochloraz, prothioconazole, pyraclostrobin, pyribencarb, sedaxane, SYP-1620, SYP-Z048 tebuconazole, thiabendazole, thiophanate-methyl, thiram, triadimenol, triazoxide, trifloxystrobin and triticonazole.

3. The method according to claim 1, further comprising applying to the plant propagation material at least one insecticide selected from the group consisting of thiamethoxam, clothianidin, imidacloprid, thiacloprid, acetamiprid, beta-cyfluthrin, cyantraniliprole, diafenthiuron, diazinon, emamectin, emamectin benzoate, fenoxycarb, fipronil, flonicamid, lambda-cyhalothrin, methiocarb, pymetrozine, pyriproxyfen, pyrifluquinazon, spinetoram, spinosad, spirotetramat, tefluthrin, thiodicarb and Ti-435.

4. The method according to claim 1, further comprising applying to the plant propagation material at least one synthetic nematicide selected from the group consisting of an avermectin nematicide; a carbamate nematicide, and an organophosphorus nematicide.

5. The method according to claim 4, further comprising applying to the plant propagation material at least one synthetic nematicide selected from the group consisting of abamectin, aldicarb, thiadicarb, carbofuran, carbosulfan, oxamyl, aldoxycarb, ethoprop, methomyl, benomyl, alanycarb, fenamiphos, fensulfothion, terbufos, fosthiazate, dimethoate, phosphocarb, dichlofenthion, isamidofos, fosthietan, isazofos ethoprophos, cadusafos, terbufos, chlorpyrifos, dichlofenthion, heterophos, isamidofos, mecarphon, phorate, thionazin, triazophos, diamidafos, fosthietan and phosphamidon.

* * * * *